United States Patent [19]

Bremer et al.

[11] Patent Number: 4,563,439

[45] Date of Patent: * Jan. 7, 1986

[54] PREPARATION OF MIXED VANADIUM PHOSPHORUS OXIDE CATALYSTS

[75] Inventors: Noel J. Bremer, Kent; Dennis E. Dria, Cleveland Heights, both of Ohio

[73] Assignee: The Standard Oil Company, Cleveland, Ohio

[ * ] Notice: The portion of the term of this patent subsequent to Aug. 2, 2000 has been disclaimed.

[21] Appl. No.: 640,641

[22] Filed: Aug. 14, 1984

Related U.S. Application Data

[63] Continuation of Ser. No. 488,902, Apr. 27, 1983, Pat. No. 4,465,846, which is a division of Ser. No. 320,780, Nov. 12, 1981, Pat. No. 4,396,535.

[51] Int. Cl.$^4$ .................... B01J 27/198; B01J 27/188; B01J 27/19; B01J 27/192
[52] U.S. Cl. .................... 502/209; 502/210; 502/211; 502/212; 502/213
[58] Field of Search ............... 502/209, 210, 211, 212, 502/213

[56] References Cited

U.S. PATENT DOCUMENTS

| | | | |
|---|---|---|---|
| 4,016,105 | 4/1977 | Ken ........................ | 502/209 |
| 4,052,417 | 10/1977 | Slinkard et al. ................ | 502/209 X |
| 4,116,808 | 9/1978 | Mount et al. .................... | 502/209 X |
| 4,171,316 | 10/1979 | Pedersen .......................... | 502/209 X |
| 4,222,945 | 9/1980 | Higgins et al. .................. | 502/209 X |
| 4,225,465 | 9/1980 | Bremer .................. | 502/209 |
| 4,293,498 | 10/1981 | Lemanski et al. .............. | 502/209 X |
| 4,360,453 | 11/1982 | Lemanski et al. .................... | 502/209 |
| 4,416,802 | 11/1983 | Udovich et al. .................... | 502/209 |

*Primary Examiner*—John Doll
*Assistant Examiner*—William G. Wright
*Attorney, Agent, or Firm*—Charles S. Lynch; John E. Miller; Larry W. Evans

[57] ABSTRACT

Vanadium phosphorus mixed oxide containing catalysts are prepared by sequentially forming an alpha-VOPO$_4$ catalyst precursor in aqueous media, and thereafter partially reducing a portion of the vanadium to a valence state of +4 in an organic liquid reducing media, in the absence of corrosive reducing agents. The catalysts exhibit excellent activity for the production of maleic anhydride from 4 carbon atom hydrocarbons such as n-butane.

8 Claims, No Drawings

PREPARATION OF MIXED VANADIUM PHOSPHORUS OXIDE CATALYSTS

This application is a continuation of application Ser. No. 488,902, filed Apr. 27, 1983, now U.S. Pat. No. 4,465,846, which in turn was a division of application Ser. No. 320,780 filed Nov. 12, 1981, now U.S. Pat. No. 4,396,535.

BACKGROUND OF THE INVENTION

This invention relates to a method for preparing catalysts useful in the oxidation of hydrocarbons. More particularly it is directed to the preparation of catalysts suitable for the production of dicarboxylic acid anhydrides from hydrocarbons, such as the production of maleic anhydride from 4-carbon atom hydrocarbons, such as n-butane, n-butenes, 1,3-butadiene or a mixture thereof.

Catalysts containing vanadium and phosphorus oxides have been used in the oxidation of 4-carbon atom hydrocarbons, such as n-butane, n-butenes, 1,3-butadiene or mixtures thereof with molecular oxygen or oxygen-containing gas to produce maleic anhydride. Conventional methods of preparing these catalysts involve reducing a pentavalent vanadium compound, and combining the same with a phosphorus compound and, if desired, promoter element compounds under conditions which will provide or maintain vanadium in a valence state below +5 to form catalyst precursors capable of being converted to an oxide. The catalyst oxide precursor is then recovered and calcined to provide active catalytic material.

U.S. Pat. No. 3,985,775 describes the preparation of vanadium phosphorus catalysts in an aqueous solution of concentrated hydrochloric acid. This patent also describes the catalyst preparation in non-aqueous media, where corrosive reducing agents were added to the media or were generated in situ.

The use of gaseous HCl as a reducing agent for vanadium is disclosed in U.S. Pat. No. 4,002,650 where the vanadium and phosphorus components are reacted in an aqueous solution. The use of gaseous HCl as a reducing agent for vanadium is also described in U.S. Pat. No. 4,043,943 where the vanadium and phosphorus components are reacted in a liquid organic medium.

U.S. Pat. No. 4,016,105 describes the preparation of vanadium and phosphorus oxide-containing catalysts, utilizing as reducing agents, organic acids or aldehydes, together with a co-reducing secondary alcohol. These reducing agents are added to an aqueous solution with the vanadium and phosphorus components.

Similar preparational techniques are described in European Patent Application No. 3,431 in which the additional step of comminuting the vanadium-phosphorus precursor to a particle size of 500 to 700 microns (0.5 to 0.7 mm) is disclosed.

The use of such reducing agents as disclosed in the art requires special precautions in the preparation of these catalysts because of the corrosive nature of the materials utilized. The process of the present invention permits the preparation of mixed vanadium phosphorus oxide catalyst without the use of corrosive reducing agents.

A method for preparing catalysts containing vanadium and phosphorus oxides was described in U.S. Pat. No. 4,132,670, which required the maintenance of a solid phase and dispersion of the vanadium-containing feed compound. The method includes forming a vanadium-containing compound dispersion in an organic liquid medium such as alcohols, aldehydes, ketones, ethers or mixtures thereof, heating the dispersion to reduce the vanadium, and thereafter adding phosphoric acid in an organic solvent.

The preparation of oxidation catalysts containing the mixed oxides of vanadium and phosphorus is disclosed in U.S. Pat. No. 4,244,879 wherein a vanadium compound is at least partially solubilized in an organic liquid medium capable of reducing at least a portion of the vanadium to a +4 valence state, and unsolubilized vanadium having a particle size larger than about 0.1 mm diameter is removed from the medium before addition of a phosphorus-containing compound.

The preparation of vanadium phosphorus mixed oxide containing catalysts is disclosed in co-pending U.S. Ser. No. 146,971, assigned to our common assignee, wherein partial reduction of a pentavalent vanadium compound is effected in the presence of a phosphorus compound in an organic liquid medium capable of reducing the vanadium.

Co-pending U.S. Ser. No. 220,629, now U.S. Pat. No. 4,361,501, also assigned to our common assignee, discloses the preparation of vanadium phosphorus oxide catalysts utilizing a mixed phosphorus component compound source, preparing the catalyst in a liquid medium capable of reducing the vanadium component.

Generally, the preparation of vanadium phosphorus mixed oxide containing catalysts in organic media rather than aqueous media, resulted in the production of catalysts having higher activity for oxidation reactions, such as the oxidation of n-butane to produce maleic anhydride. The organic-derived vanadium phosphorus mixed oxide catalysts additionally exhibit higher intrinsic surface area than the aqueous-derived vanadium phosphorus mixed oxide catalysts. Although the use of organic preparative media capable of properly reducing the vanadium component of the catalyst alleviated the need to employ corrosive reducing agents with their attendant costs and difficulties, the commercial use of a total organic preparation would be less desirable than a method of preparation which limited the use of organic materials to critical processing steps.

DISCLOSURE OF THE INVENTION

We have found that vanadium phosphorus mixed oxide containing catalysts exhibiting excellent hydrocarbon oxidation activity can be prepared by a process which includes the formation of a substantially pentavalent alpha-VOPO$_4$ catalyst precursor in aqueous media. The alpha-VOPO$_4$ catalyst precursor is then subjected to vanadium reduction in a substantially organic liquid medium capable of reducing at least a portion of the vanadium to a +4 valence state. This approach is contrary to teachings of the prior art, which teachings generally instruct the reduction of vanadium prior to formation of a vanadium-phosphorus precursor.

The catalysts prepared by the method of the present invention exhibit excellent activity for hydrocarbon oxidation reactions, such as the production of maleic anhydride from 4-carbon atom hydrocarbons, particularly n-butane.

It is therefore an object of the invention to provide a process for preparing vanadium and phosphorus mixed oxide-containing catalysts useful for the oxidation of 4-carbon atom hydrocarbons such as n-butane to produce maleic anhydride, which catalysts exhibit excellent yields and selectivity to maleic anhydride.

It is a further object of the invention to provide a process for preparing vanadium and phosphorus-containing catalysts useful for the oxidation of 4-carbon atom hydrocarbons such as n-butane, to produce maleic anhydride, which process is simplified, highly reproducible, and economical; which process avoids the hazards of corrosion, and which is capable of commercial scale-up.

In general, the process of the present invention includes
(a) introducing a pentavalent vanadium compound and a pentavalent phosphorus compound into an aqueous medium;
(b) forming a pentavalent, alpha-$VOPO_4$ catalyst precursor in the aqueous medium;
(c) recovering the pentavalent catalyst precursor from the aqueous medium.
(d) introducing the pentavalent catalyst precursor into a substantially organic liquid medium capable of reducing at least a portion of the vanadium to a valence state of about +4 in the absence of corrosive reducing agents;
(e) effecting reduction of the vanadium;
(f) recovering the resulting partially reduced catalyst precursor from the organic liquid medium;
(g) drying the partially reduced catalyst precursor;
(h) calcining the partially reduced catalyst precursor.

The catalysts prepared by the above process are particularly effective in the oxidation of 4-carbon atom hydrocarbons such as n-butane, n-butenes, 1,3-butadiene or mixtures thereof with molecular oxygen or an oxygen-containing gas in the vapor phase to produce high yields of maleic anhydride with high selectivity. Essentially all the product produced in this oxidation process is maleic anhydride, with only minor amounts of lower acids being detected.

DETAILED DESCRIPTION OF THE INVENTION

In the present process for the preparation of an oxidation catalyst containing the mixed oxides of vanadium and phosphorus, a pentavalent vanadium compound and a phosphorus compound, also preferably pentavalent, are introduced into an aqueous medium.

Suitable vanadium compounds containing pentavalent vanadium include vanadium pentoxide and ammonium metavanadate. Suitable pentavalent phosphorus compounds include: phosphoric acid, phosphorus pentoxide or a mixed pentavalent phosphorus component comprising a mixture of orthophosphoric acid and pyrophosphoric acid. Optionally, minor amounts of higher polyphosphoric acid may be included. If a mixed phosphorus source is desired, the phosphorus component mixture should comprise about 45 to about 90 percent orthophospohoric acid, about 10 to about 50 percent pyrophosphoric acid, and 0 to about 10 percent triphosphoric acid and higher polyphosphoric acids, percentages being based upon weight of total phosphoric acids. As hydrolysis is a factor in determining the ratio of orthophosphoric acid to pyrophosphoric acid when present in aqueous solution, the above weight ratios are significant provided an extended period of hydrolysis has not occurred to convert the pyrophosphoric acid and higher polyphosphoric acids to the orthophosphoric form.

The aqueous medium liquid may consist essentially of water, such that the medium comprises an aqueous solution or slurry of catalyst component element containing compounds including compounds containing vanadium, phosphorus, and promoter metal elements, if any. The aqueous medium should be free from agents which would substantially reduce the pentavalent vanadium component.

The manner of introduction of the pentavalent vanadium and phosphorus compounds into the aqueous medium may vary. For example, both may be introduced into water or an aqueous solution or slurry together, the phosphorus component may be introduced into an aqueous solution or slurry of the vanadium compound, or the vanadium compound may be introduced into an aqueous solution of a phosphorus compound.

The substantially pentavalent, alpha-$VOPO_4$ catalyst precursor may be formed in the aqueous medium by heating the medium, preferably under reflux conditions. The pentavalent catalyst precursor may be recovered by conventional methods, such as evaporation, precipitation and filtration, centrifugation, and the like.

After recovery, the pentavalent alpha-$VOPO_4$ catalyst precursor is introduced into the organic liquid medium for reduction of the vanadium. The organic liquid medium employed in the process of the present invention must be capable of reducing at least a portion of the vanadium to a +4 valence state, preferably upon mixing and heating. The organic liquid medium should not, however, be a solvent for the mixed oxide precursor of vanadium and phosphorus and thus the medium is maintained free of corrosive reducing or solubilizing agents such as HCl, HBr and oxalic acid.

Suitable organic liquid media for use in the invention include alcohols, aldehydes, ethers, glycols, ketones, halogenated olefins, mixtures thereof, and are preferably anhydrous. Suitable alcohols may be primary or secondary, saturated or unsaturated. Examples of organic liquids suitable for use in this invention include but are not limited to isopropanol, isobutanol, sec-butanol, allyl alcohol, crotyl alcohol, acetaldehyde, methyl ethyl ketone, ethylene glycol, dibutyl ether, hexachlorobutadiene, perchloropropene, and the like.

The reduction of the vanadium is preferably effected by heating the precursor containing organic liquid medium, with stirring if desired. Preferred vanadium and phosphorus oxide catalysts for the oxidation of 4-carbon atom hydrocarbons to maleic anhydride contain vanadium in an average valence state of about +3.5 to about +4.6. This average valence state is achieved when at least a portion of the pentavalent vanadium present in the organic liquid medium is reduced to the +4 state. The average valence state of the vanadium is reduced preferably to about +4.1. In one embodiment of this invention, during the reduction of the vanadium in the organic liquid medium with heating under reflux conditions, at least 1.5 moles organic liquid per mole of vanadium reacted is removed by distillation during the reaction of the vanadium, as taught by U.S. Ser. No. 286,434, assigned to our common assignee herein.

During reduction of the vanadium in the alpha-$VOPO_4$ containing organic liquid medium, the partially reduced vanadium phosphorus mixed oxide catalyst precursor is formed. After the partially reduced catalyst precursor is formed, it is recovered from the reaction medium by conventional methods including evaporation, filtration, centrifugation and decantation. The partially reduced catalyst is dried, generally at temperatures between about 100° C. to about 175° C. and is thereafter calcined.

It is within the scope of this invention, to include promoter element-containing compounds in the catalyst at a suitable point, such as either by introducing the promoter element containing compounds in the aqueous medium or in the organic liquid medium, prior or subsequent to the reduction of the vanadium, in order that the partially reduced catalyst precursor contain the promoter element. Additionally, promoter elements may be added to the catalyst precursor after drying or to the catalyst after calcination. Suitable promoters include but are not limited to Tl, Cr, W, Nb, Ta, Mn, Th, U, Co, Mo, Fe, Zn, Hf, Zr, Ni, Cu, As, Sb, Te, Bi, Sn, Ge, Cd, the lanthanides or mixtures thereof. Suitable promoter element containing compounds include metal oxides, hydroxides, and salts such as nitrates, carbonates, acetates and the like.

Catalysts produced by the process of this invention are prepared preferably to exhibit a phosphorus to vanadium ratio of about 0.8:1 to about 1.3:1. The molar ratio of promoter to vanadium is generally between about 0.01 to about 0.5. The catalyst is generally calcined in an inert atmosphere, air or an oxygen-containing gas at a temperature of about 250° C. to about 600° C. Calcination of the catalyst may also be accomplished by heating the catalyst in a mixture of steam and air or air alone at a temperature of about 300° C. to about 500° C. The catalyst may also be calcined either in the presence of hydrocarbon, an inert gas, or both.

The hydrocarbon reacted to form maleic anhydride may be n-butane, the n-butenes, 1,3-butadiene or a mixture thereof. Preferred is the use of n-butane or a mixture of hydrocarbons that are produced in refinery streams. The molecular oxygen needed for the reaction to produce maleic anhydride is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely. The ratio of molecular oxygen to the hydrocarbon may range from about 3 to about 30 moles of oxygen per mole of hydrocarbon. Preferred oxygen/hydrocarbon ratios are about 4 to about 20 moles of oxygen per mole of hydrocarbon.

The reaction temperature may vary widely and is dependent upon the particular hydrocarbon and catalyst employed. Normally, temperatures of about 250° C. to about 600° C. are employed with temperatures of about 325° C. to about 475° C. being preferred.

The catalyst may be used alone or a catalyst support could be employed. Suitable supports include silica, alumina, silica-alumina, Alundum, silicon carbide, titania, boron phosphate, zirconia, and the like. The catalyst may be used in a fixed-bed reactor using tablets, pellets or the like, or in a fluid-bed reactor using catalysts prepared such as by oil dropping or by spray drying, and preferably having a particle size of less than about 300 microns. The contact time may be as low as a fraction of a second or as high as 50 seconds. The reaction may be conducted at atmospheric, superatmospheric or subatmospheric pressure.

SPECIFIC EMBODIMENTS OF THE INVENTION

Examples 1–3

Catalysts of the formula $V_1P_{1.16}O_x$ (where x is the number of oxygens needed to satisfy the valence requirements of the other elements) were prepared as follows. 90.95 g $V_2O_5$ were added to 1.34 g $H_3PO_4$ (85% aqueous) with stirring and slight heating. The resulting slurry of alpha-$VOPO_4$ was heated to evaporation and dryness at about 150° C. for 16 hours. The dried alpha-$VOPO_4$ precursor was crushed and introduced into about 700 ml isobutanol. The resulting slurry was heated under reflux conditions for about 16 hours.

The partially reduced catalyst precursor, a light blue fine precipitate, was filtered from the organic liquid medium, and about 55 g was dried at 100° C. for about 1 hour and then at 150° C. for about 1 hour. The dried precursor was calcined in air at 400° C. for about 1.5 hours. About 40 g of the calcined catalyst was mixed with about 1.2 g stearic air processing aid and was tabletted to form 3/16 inch diameter (0.48 cm) tablets. The catalysts were tested for butane oxidation to maleic anhydride according to the procedure set forth below.

Examples 4–6

Catalysts of the formula $V_1P_{1.16}O_x$ were prepared as follows. 90.95 g $V_2O_5$ and 133.8 g $H_3PO_4$ (85% aqueous) were added to 1200 ml water with stirring. The mixture was heated to reflux for about 16 hours. An additional 268 g $H_3PO_4$ (85%) was added with refluxing to precipitate out the alpha-$VOPO_4$ catalyst precursor. The resulting alpha-$VOPO_4$ precipitate was recovered by filtration, and was heated to dryness at 150° C.

About 110 g of the alpha-$VOPO_4$ precursor was introduced into 1200 ml isobutanol, and heated to reflux to effect vanadium reduction. The resulting partially reduced blue catalyst precursor precipitate was recovered by filtration and heated to dryness at about 150° C. 50 g of the partially reduced catalyst precursor was calcined in air at about 400° C. for one hour. About 42.5 g of the calcined catalyst was mixed with a tabletting processing aid and was tabletted to form 3/16 inch diameter (0.48 cm) tablets. The catalysts were tested for butane oxidation to maleic anhydride according to the procedure set forth below.

Comparative Examples 7 and 8

Catalysts of the formula $V_{1.0}P_{1.15}O_x$ were prepared according to the prior art method described above, in which the catalyst precursor is formed by reducing vanadium in a corrosive reducing agent-containing aqueous medium. 33.6 g of vanadium pentoxide were digested in 437.5 mls. of concentrated hydrochloric acid and refluxed for 3 to 4 hours. To this mixture was added 48.65 g of 85% phosphoric acid and refluxing was continued an additional 6 hours. The resulting mixture was evaporated to dryness, and dried overnight at 110° C. Calcination was conducted for 1 hour at 360° C. in air. The resulting catalysts were tested for butane oxidation to maleic anhydride according to the procedure set forth below. These catalysts were much less active as compared to catalysts prepared by the method of the present invention, requiring higher operating temperatures and higher air/hydrocarbon ratios, yet providing lower yields of product.

Comparative Examples 9 and 10

Catalysts of the formula $V_1P_{1.16}O_x$ were prepared by heating a mixture of 90.95 g $V_2O_5$ and 133.74 g $H_3PO_4$ (85% aqueous). To the pentavalent precursor was added the reducing agent 13 g $N_2H_4 \cdot H_2O$ in 20 ml water with heating. The vanadium was reduced to a valence state of about +4, and the resulting blue precipitate was filtered, washed with water and dried for 2 hours at 150° C. The catalyst precursor was calcined at 400° C. for about 75 minutes, and tested for butane oxidation to maleic anhydride by the procedure set forth below. The catalysts prepared by sequentially forming a pentavalent $VOPO_4$ precursor and reducing the precursor with an inorganic reducing agent resulted in a catalyst having poor oxidation properties for production of maleic anhydride from n-butane.

Catalyst Testing

The catalysts described in Examples 1–10 were tested for the production of maleic anhydride from n-butane using a 20 cc fixed-bed reactor consisting of a 38 cm length of stainless steel tubing having an outer diameter of about 1.3 cm and having a full length 0.31 cm axial thermowell. The reactor was heated with a split stainless steel block furnace. Flasks for receiving the product maleic anhydride were mounted in ice water, and tail gases were routed to a gas chromatograph for analysis. Reaction conditions and results of the tests run are described in Table I. The results are stated in terms as follows:

$$\text{Single Pass Yield} = \frac{\text{Moles of Maleic Anhydride Formed}}{\text{Moles of Butane Fed}} \times 100$$

$$\text{Total Conversion} = \frac{\text{Moles of Butane Reacted}}{\text{Moles of Butane Fed}} \times 100$$

$$\text{Selectivity} = \frac{\text{Single Pass Yield}}{\text{Total Conversion}}$$

TABLE I

OXIDATION OF N—BUTANE TO MALEIC ANHYDRIDE OVER VANADIUM PHOSPHORUS MIXED OXIDE CATALYSTS

| Example No. | Air/HC Ratio | Temperature °C. | Contact Time (Sec.) | % Conversion | Maleic Anhydride % Yield | % Selectivity |
|---|---|---|---|---|---|---|
| 1 | 53.5 | 403 | 2 | 96.9 | 58.9 | 60.8 |
| 2 | 52 | 393 | 2 | 85.4 | 56.7 | 66.5 |
| 3 | 66.6 | 414 | 2 | 85.0 | 54.8 | 64.5 |
| 4 | 62.9 | 415 | 1 | 92.1 | 55.2 | 60.0 |
| 5 | 61 | 390 | 2 | 93.8 | 60.1 | 64.1 |
| 6 | 61.4 | 398 | 2 | 84.5 | 56.1 | 66.4 |
| C7 | 112 | 499 | 1.3 | 55.8 | 30.4 | 54.5 |
| C8 | 108 | 513 | 1.4 | 67.5 | 31.8 | 47.1 |
| C9 | 64 | 400 | 1 | 5 | — | — |
| C10 | 64 | 500 | 1 | 35 | 8 | 22 |

The results reported in the Table demonstrate that vanadium and phosphorus mixed oxide containing catalysts prepared by sequentially forming an alpha-$VOPO_4$ catalyst precursor in aqueous media, and thereafter partially reducing the vanadium present in the precursor in an organic liquid medium, in the absence of corrosive reducing agents, results in a catalyst exhibiting excellent activity for the oxidation of hydrocarbons, particularly, the production of maleic anhydride from 4-carbon atom hydrocarbons such as n-butane.

Thus it should be apparent to those skilled in the art that the subject invention accomplishes the objects set forth above. It is to be understood that the subject invention is not to be limited by the examples set forth herein. These have been provided merely to demonstrate operability, and the selection of vanadium compounds, phosphorus compounds, reducing organic liquid media, promoter element-containing compounds, if any, hydrocarbon feedstocks and reaction conditions can be determined from the total specification disclosure provided without departing from the spirit of the invention herein disclosed and described, the scope of the invention including equivalent embodiments, modifications and variations that fall within the scope of the attached claims.

We claim:

1. A vanadium/phosphorus mixed oxide catalyst precursor composition prepared by contacting and heating in an aqueous medium a pentavalent vanadium compound with phosphoric acid and forming a substantially pentavalent, alpha $VOPO_4$ catalyst precursor in the aqueous medium, wherein the aqueous medium is free from agents which would substantially reduce the pentavalent, alpha $VOPO_4$ catalyst precursor, recovering the pentavalent catalyst precursor from the aqueous medium and introducing the pentavalent catalyst precursor into a substantially organic liquid medium capable of reducing at least a portion of the vanadium to a valence state of about +4.

2. A catalyst precursor composition of claim 1 wheein said organic liquid medium comprises an alcohol.

3. A catalyst precursor composition of claim 1 wherein said organic liquid medium comprises isobutanol.

4. A process for making a vanadium/phosphorus mixed oxide catalyst precursor composition prepared by contacting and heating in an aqueous medium a pentavalent vanadium compound with phosphoric acid and forming a substantially pentavalent, alpha $VOPO_4$ catalyst precursor in the aqueous medium, wherein the aqueous medium is free from agents which would substantially reduce the pentavalent, alpha $VOPO_4$ catalyst precursor, recovering the pentavalent catalyst precursor from the aqueous medium and introducing the pentavalent catalyst precursor into a substantially organic liquid medium capable of reducing at least a portion of the vanadium to a valence state of about +4.

5. A process as in claim 4 wherein said organic liquid is selected from alcohols, ethers, glycols, ketones, halogenated olefins, and mixtures thereof.

6. A process as in claim 4 wherein said organic liquid is selected from isopropanol, isobutanol, sec-butanol, allyl alcohol, crotyl alcohol, acetaldehyde, methyl ethyl ketone, ethylene glycol, dibutyl ether, hexachlorobutadiene and perchloropropene.

7. A process as in claim 4 wherein said organic liquid comprises an alcohol.

8. A process as in claim 4 wherein said alcohol comprises isobutanol.

* * * * *